(12) United States Patent
Pang et al.

(10) Patent No.: US 12,098,393 B2
(45) Date of Patent: Sep. 24, 2024

(54) MAMMAL-SPECIFIC GROWTH-DEFECTIVE ARBOVIRUS

(71) Applicants: Xiaowu Pang, Bethesda, MD (US); Xinbin Gu, Bethesda, MD (US)

(72) Inventors: Xiaowu Pang, Bethesda, MD (US); Xinbin Gu, Bethesda, MD (US)

(73) Assignee: Tengen Biomedical Company, Bethesda, MD (US)

( * ) Notice: Subject to any disclaimer, the term of this patent is extended or adjusted under 35 U.S.C. 154(b) by 414 days.

(21) Appl. No.: 16/645,788

(22) PCT Filed: Sep. 11, 2018

(86) PCT No.: PCT/US2018/050341
§ 371 (c)(1),
(2) Date: Mar. 9, 2020

(87) PCT Pub. No.: WO2019/051445
PCT Pub. Date: Mar. 14, 2019

(65) Prior Publication Data
US 2021/0222132 A1 Jul. 22, 2021

Related U.S. Application Data

(60) Provisional application No. 62/556,892, filed on Sep. 11, 2017.

(51) Int. Cl.
*C12N 7/00* (2006.01)

(52) U.S. Cl.
CPC ...... *C12N 7/00* (2013.01); *C12N 2710/12034* (2013.01); *C12N 2770/24122* (2013.01); *C12N 2770/24134* (2013.01); *C12N 2770/24151* (2013.01); *C12N 2770/36134* (2013.01)

(58) Field of Classification Search
None
See application file for complete search history.

(56) References Cited

U.S. PATENT DOCUMENTS

| | | |
|---|---|---|
| 10,040,824 B2 | 8/2018 | Pang et al. |
| 2009/0004721 A1 | 1/2009 | Keelepang et al. |
| 2012/0263754 A1 | 10/2012 | Dubensky et al. |
| 2017/0252425 A1 | 9/2017 | Akahata et al. |

OTHER PUBLICATIONS

Keelapang et al., "Alternations . . . viruses," J Virol 78(5)2367-2381, 2004.
Konishi et al., "Generation . . . particles," J Virol 75(3)204-2212, 2001.

*Primary Examiner* — Stacy B Chen
(74) *Attorney, Agent, or Firm* — MDIP LLC

(57) ABSTRACT

Arbovirus carries an altered furin cleavage site that results in enhanced cleavage of a precursor polyprotein, such as, prE2 or prM. Dengue virus particles can have an amino acid alteration within amino acids 80-130 of prM. Zika virus particles can have alterations at amino residues at and/or about the furin cleavage site. The virus can be produced in insect cells. The virus does not form progeny virus in mammal cells.

13 Claims, 3 Drawing Sheets

Specification includes a Sequence Listing.

Protection test with AG129 mice

- M2-ZIKV
- PBS

Percent survival vs Days (5, 10, 15)

Figure 2

MAMMAL-SPECIFIC GROWTH-DEFECTIVE ARBOVIRUS

BACKGROUND OF THE INVENTION

The invention relates generally to arboviruses, a small group of a few viruses with the unique and unusual property of replicating in insect cells and in human cells. The present invention relates to mutated arboviruses and use thereof as immunogens. In aspects, the present invention relates to altered arbovirus that no longer reproduces in mammal host cells, but continues to replicate in insect cells and can be harvested therefrom, yet continues to express and to present arbovirus antigens in and to the mammal immune system.

The instant invention relates to the arbovirus group of viruses. A basic property of arbovirus is replication in mammal and in insect cells. Many arboviruses are transmitted to mammals by ticks or by mosquitoes. Under one classification scheme, arboviruses include the genera, Flavivirus, Alphavirus and Orthobunyavirus. Under another classification scheme, arboviruses include the families, Bunyaviridae, Flaviviridae, Reoviridae and Togaviridae. Examples of arboviruses include African Swine Fever virus, Tick-borne Encephalitis virus, Rift Valley Fever virus, Colorado Tick Fever virus, Equine Encephalosis virus, Chikungunya virus, Dengue virus (DV), Zika virus (ZV) and West Nile virus.

Flaviviruses have been studied, in part, because of human pathology, see, for example, Gubler & Kuno, eds.: Dengue and Dengue Hemorrhagic Fever. Wallingford, CAB International, 1997; and Porterfield: Exotic Viral Infections. Chapman and Hall Medical, London, 1995.

Flavivirus genomes consist of a single linear, single-stranded, +sense RNA. The +strand RNA infects appropriate host cells. The total genome can range from 10 to 11 kbs. There is no 3' polyadenylation. The 5' end has a methylated cap.

Flavivirus genomes do not contain internal ribosomal entry sites (IRES) that provide a site of translation initiation for host ribosomes. Instead, flavivirus employs ribosomal scanning to commence protein synthesis.

Flavivirus virions can be spheres, 40-65 nm in diameter. Under the lipid envelope is an icosahedral capsid coat approximately 25-30 nm in diameter.

DV (types 1-5), Yellow Fever virus, Japanese Encephalitis virus, Tick-borne Encephalitis virus and West Nile virus are causative agents of significant morbidity and mortality in humans.

For example, the Yellow Fever virus is capable of causing epidemics. In the first cycle, virus is transmitted by *Aedes africanus* and other *Aedes* mosquitoes (in Africa) or by Hemogogus mosquitoes (in the Americas): monkeys serve as the reservoir, and generally, humans infected are those who enter deep forests and jungles, and are exposed to those vectors. In the second cycle, the domestic mosquito, *Aedes aegypti*, which lives in close relationship with humans, may transmit the virus directly to humans, the sole host in the cycle.

Flaviviruses cause other diseases, such as, Murray Valley Encephalitis, Rocio and Powassan Encephalitis, and as more recently observed in the Americas, West Nile fever and Zika fever.

Several flaviviruses, including Louping Ill virus that causes neurologic disease in sheep, West Nile virus that causes encephalitis in horse and Japanese Encephalitis virus that also causes encephalitis in horses as well as stillbirth in pigs, are veterinary pathogens of commercial importance.

Considering the urgent need for arbovirus treatments, a robust method for making safe and effective arbovirus treatment compositions is needed. Theoretically, live attenuated vaccines elicit the most effective, long-term, specific immunity, whereas inactivated virus vaccines, including recombinant subunit vaccines, provide higher levels of safety. The ideal vaccine would be one that can produce the efficacy of live vaccine and the safety of subunit vaccine.

Those goals were achieved in development of a scalable method for making mammal-specific growth-restricted arboviruses. The growth-defective virus of interest resides in and expresses arbovirus antigens and elicits an immune response in infected mammals to arbovirus antigen(s) but does not produce progeny virus in mammal cells so an infected cell does not contribute to radiating cell infection and pathology in a mammal host. Propagation of the growth-restricted virus of interest is not disturbed in insect cells. Thus, a dysfunctional virus of interest can be produced economically in insect cell lines.

SUMMARY OF THE INVENTION

The inventions relate to materials and methods for making growth-restricted arbovirus particles that continue to replicate in insect cells but no longer replicate (or do so at low levels) in mammal cells (such as, human cells), so infected mammal cells do not produce progeny virus. The arbovirus of interest infects a host mammal cell, can replicate in that host mammal cell to produce arbovirus proteins that are recognized by the mammal host immune system, for example, with cellular and/or humoral responses, but does not produce and does not release progeny arbovirus particles. The defective virus of interest comprises all the necessary genes to ensure viral genome replication and production of arbovirus proteins, which can be released from the infected cell or can be expressed at the surface of the host cell, but does not produce progeny virus from the infected host mammal cell. Thus, arbovirus particles of interest can be as immunogenic as wild-type virus, but the particles should not contribute much, if at all, to disease or pathology in the infected host because the altered arbovirus of interest presents with diminished, if any, replication in mammal cells.

The growth-restricted arbovirus of interest do not propagate readily in mammal or human cells, producing and releasing a reduction in virus particles of 4 logs or less, 5 logs or less, 6 logs or less, 7 logs or less, 8 logs or less, 9 logs or less, or no progeny arbovirus as compared to the level or amount of progeny virus produced in the same type of cell infected by wild-type arbovirus of the same species or of a sample prior to treatment to become growth-restrictive.

On the other hand, the growth-restricted or growth-defective arbovirus of interest propagates readily in insect cells, such as, arthropod cells, to produce like progeny arbovirus. The level of progeny arbovirus produced by an insect cell can be about equal to or can exceed levels or amounts of progeny virus produced by a suitable, control wild-type arbovirus of the same species or of a sample used for treatment to become growth-restrictive in that same insect cell.

In embodiments, a defective arbovirus of interest comprises enhanced (that is, may cleave at a higher rate, may cleave more efficiently or both, as compared to wild type arbovirus of the same species or of a sample prior to treatment to become growth-restrictive) furin activity. Furin cleavage of a precursor polyprotein can be essential to arbovirus progeny particle maturation. In some arboviruses, furin cleavage occurs at the juncture of pr and M. Hence, a defective arbovirus of interest comprises enhanced furin activity at, in or about the prM protein or polypeptide. In some arboviruses, furin cleavage occurs at the juncture of E3 and E2. Hence, a defective arbovirus of interest comprises enhanced furin activity at, in or about the precursor E2 protein or polypeptide.

A growth restricted arbovirus of interest comprises an alteration at the furin consensus tetrapeptide, which may be at the juncture of, for example, pr and M: an alteration upstream of the consensus tetrapeptide (amino terminal direction, for example, in pr polypeptide): an alteration downstream of the consensus tetrapeptide (carboxy terminal direction, for example, in M protein): or combinations thereof.

In embodiments, the arbovirus is a Dengue virus (DV), which comprises a prM polyprotein.

In embodiments, one or more amino acid substitutions in and/or about the furin cleavage site between pr and M results in a virus with enhanced furin cleavage of prM; propagates in insect cells; and does not propagate in mammal or human cells.

In embodiments, the enhanced furin activity in DV is obtained by one or more of: 1) an alteration in the eight amino acid stretch upstream (in direction of the amino terminus) of the furin recognition and cleavage site beginning at amino acid 80 of the prM polypeptide of DV, that is amino acids 80-87 of prM: 2) an alteration in the tetrapeptide furin recognition site: 3) an alteration in the thirty-nine amino acid stretch downstream (in direction of the carboxy terminus) of the furin recognition and cleavage site, that is, amino acids 92-130 of prM: 4) an alteration upstream of amino acid 80; and 5) an alteration downstream of amino acid 130. Any combination of the above can be present, for example, 1), 2) and 3) can be present. Alterations 1), 2) and 3) can be present.

In embodiments, the DV furin cleavage site in the prM protein, $NH_2$-(88)Arg-Glu-Lys-Arg-COOH/(SEQ ID NO:1), where cleavage occurs after the Lys-Arg residues (and is indicated by the "/" in the cleavage recognition site denoted above), is altered at the Glu site to enhance furin cleavage.

In embodiments, Glu is replaced by any amino acid.

In embodiments, the amino acid that replaces Glu is a non-acidic, non-neutral amino acid, such as, Gln, Asn, Gly, Lys, Arg, His, Thr, Ser, Tyr, Met or Cys. In embodiments, the replacement amino acid does not contain sulfur. In embodiments, the replacement amino acid does not contain a hydroxyl group in the R group side chain. In embodiments, the replacement amino acid is a basic amino acid. In embodiments, the replacement amino acid is Lys, Arg or His. In embodiments, the replacement amino acid is Arg.

In embodiments, a defective DV of interest comprises one or more alterations of polypeptide sequence upstream of SEQ ID NO:1, for example, in the eight amino acids upstream of the Arg-Glu residues. In embodiments, a defective DV of interest comprises one or more alterations of polypeptide sequence downstream of SEQ ID NO:1, for example, in the thirty-nine amino acids downstream from the Lys-Arg residues. An alteration can be or in at the furin recognition or cleavage site. An alteration can be in the M protein. An alteration can be located within the first 39 amino terminal amino acids of the membrane protein. An alteration can be in the pr polypeptide. An alteration can be located within the last eight carboxy terminal amino acids of the pr polypeptide.

Such an alteration or combination of alterations reduces or negates replication, maturation and release of DV from infected mammal cells. Hence, the infected mammal cells contain and present DV antigens to the mammal host immune system, but, the infected mammal cells do not release infectious, progeny DV particles.

However, such alterations at or about the furin cleavage site do not negate replication of the DV of interest in insect cells, thereby providing a method and means for producing DV particles comprising the altered furin site disclosed herein for use to infect but not to replicate in mammal cells. Propagation in insect cells is robust, providing high virus yields, and growth or production of DV in insect cells is scalable for producing virus particles in larger volumes, amounts and reactions.

In embodiments, the arbovirus is Zika virus (ZV), which comprises a prM polyprotein.

The furin cleavage site of ZV is located after amino acid 93 of prM. In embodiments, the prM sequence upstream of and including the ZV furin recognition site, His-His-Lys-Lys-Gly-Glu-Ala-Arg-Arg-Ser-Arg-Arg/ (SEQ ID NO:2), is modified at the serine residue of the tetrapeptide furin recognition site (cleavage occurs after the fourth Arg in the sequence above) to provide a sequence of five arginine residues to enhance furin cleavage. In embodiments, the glutamic acid residue of that region may be altered to histidine to enhance furin cleavage. Other alterations can be made to the above sequence of residues. Alteration can be made upstream of amino acid 82 and/or downstream of amino acid 93.

The enhanced furin activity in ZV can be obtained by one or more of: (1) alteration of one or more amino acids upstream of the ZV furin cleavage site, for example, in the eight residue sequence beginning at amino acid residue 82 from the N-terminus of prM (i.e. amino acid residues 82-89 of prM), but can be upstream of amino acid 82: (2) alteration in the ZV furin tetrapeptide cleavage site; and (3) alteration of one or more amino acid residues downstream of the furin cleavage site, that is, amino acid 94 and downward, for example, in the 26 residue stretch of amino acids downstream of the tetrapeptide. Any combination of (1), (2) and (3) can be present.

Growth of a ZV of interest in mammal cells is minimized or substantially non-existent whereas growth of that dysfunctional ZV is insect cells is not substantially impacted.

Additional features and advantages of the present invention are described in, and will be apparent from, the following Detailed Description of the Invention and the Figures.

BRIEF DESCRIPTION OF THE FIGURES

FIG. 2 depicts a survival graph comprising data obtained from mice that received, prior to challenge with wild type SV, phosphate-buffered saline (PBS) as a control or an SV mutant of interest (M2).

DETAILED DESCRIPTION OF THE INVENTION

Figure 1:
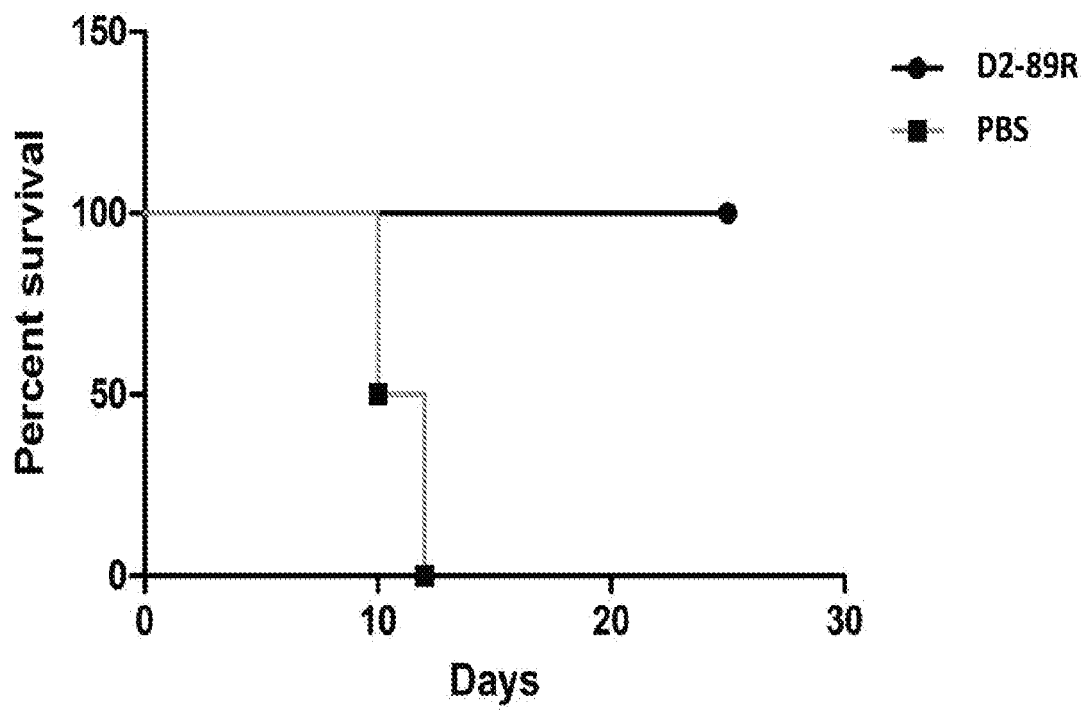
FIG. 1 depicts a survival graph comprising data obtained from mice that received, prior to challenge with wild type DV, phosphate-buffered saline (PBS) as a control or a DV mutant of interest (D2-89R).

As used herein, "dysfunction," or grammatical forms thereof, indicates an enhancement of a property or a function arising from a change or an alteration, as compared to the level of function or presence of that property observed before or without that change or alteration. For example, an enzyme site that is altered and dysfunctional may be one that is always recognized by the enzyme or is cleaved by the cognate enzyme at a greater rate, more efficiently and so on with the outcome being increased levels or amount of enzyme reaction product. For example, in embodiments, a dysfunctional furin cleavage site is cleaved at a rate or value enhanced or greater than that observed for a non-dysfunctional furin cleavage site. Hence, a decreased amount or level of prM in an infected cell is the result. A synonym of dysfunction is, "defective," or grammatic forms thereof, "Enhanced," or grammatic versions thereof, is a metric or level above a basal or a reference level or metric. A basal level can be determined by sampling a number of units and taking a mean value, or by obtaining a derived population average value from the literature. In embodiments, an enhanced level is any level higher than that found in a control sample. Hence, in a bioassay, chemical assay and the like, for example, two samples can be run, side-by side, an experimental sample suspected of an enhanced metric and a control, which can be a sample from a known wild type, normal, unaltered, non-mutated and the like representative of a population, a higher metric is revealed in the experimental sample, such as, larger amount of product, faster kinetics, a larger product and so on. In embodiments, a basal level is that which is found in a wild type unit. In embodiments, enhanced comprises an increased level of enzymic activity. In embodiments, enhanced comprises an increased level of catalytic activity. In embodiments, enhanced comprises an increased level of lytic activity. In embodiments, enhanced comprises an increased level of polypeptide cleavage by furin. In embodiments, enhanced furin activity can be revealed by comparing amounts of prM in samples from cells infected with a mutant of interest and from cells infected with a wildtype virus. In embodiments, enhanced furin activity can be revealed by reduced levels of prM or increased levels of pr or of M in a comparison of mutant and wildtype.

An, "alteration," or grammatic forms thereof, is a change or modification of a wild-type amino acid sequence, at one or more residues. Thus, an altered polypeptide can comprise an allele. The change can be an amino acid substitution, deletion or insertion, which can comprise two or more amino acids at a site of the wild type sequence. An alteration produces a dysfunctional virus of interest.

By, "stretch," or grammatic forms thereof, is meant consecutive nucleotides of a nucleic acid, or consecutive amino acids of a protein. Consecutive nucleotides of a nucleic acid (a stretch of nucleotides) are polymerized as a linear oligonucleotide. Consecutive amino acids of a protein (a stretch of amino acids) are polymerized as a linear oligopeptide.

"Propagation," or grammatic forms thereof, comprises processes where a virus infects a compatible host cell: replicates in that infected cell to produce progeny virus; and the infected cell releases the progeny virus into an extracellular space. Synonyms include, "reproduce," "replicate," "grow," and so on.

"Immunogenic," or grammatic forms thereof, comprises generating or eliciting an immune response in a host. Thus, immunogenic comprises, in embodiments, possessing an epitope or a determinant. In embodiments, for example, an immunogenic composition is one carrying an epitope or a determinant that when introduced into a host, elicits an immune response to that epitope or that determinant by the host immune system. The immune response is one which can, to some extent, "remove," the immunogenic composition from the host, where, "removing," can comprise actual destroying the composition, that is, denaturation or digestion of the composition; sequestering the composition so that the composition is contained within a structure rendering the composition inert: detoxifying the composition: neutralizing the composition: rendering the composition biologically inert: rendering the composition safe to and in the host; and so on. Immunogenic does not mean or guarantee immunoprotection in any one exposed host. The immune response can be humoral, cellular and the like, or combinations thereof.

"Does not replicate in human or mammal cells," "does not propagate in human or mammal cells," "does not grow in human or mammal cells," "does not reproduce in human or mammal cells," "is growth-restricted in human or mammal cells," "growth-restricted," "growth-defective," equivalents of those phrases, grammatic forms of those phrases and the like, are synonyms or synonymous terms or phrases, as described herein, and comprises a human or mammal cell infected with a mutant virus of interest that produces 4 logs or lower, 5 logs or lower, 6 logs or lower, 7 logs or lower, 8 logs or lower, 9 logs or lower or no progeny arbovirus as compared to the level or amount of progeny virus produced by the same type of cell infected with a wild-type arbovirus of the same species, strain, line and so on: by a like cell infected with a non-dysfunctional virus, as described herein; or by a suitable and acceptable negative control.

"Replicate in insect cells," "propagate in insect cells," "grow in insect cells," "reproduce in insect cells," "not growth-restricted in insect cells," "not growth-defective," "not growth-restricted," equivalents of those phrases, grammatic forms of those phrases and the like, are synonyms or synonymous terms or phrases, as described herein, and comprises an insect cell infected with a mutant virus of interest that produces about as much as or more progeny arbovirus as compared to the level or amount of progeny virus produced by the same type of insect cell infected with a wild type arbovirus of the same species, strain, line and so on; by a like cell infected with a non-dysfunctional virus, as described herein; or by a suitable and acceptable negative control.

"About," is an approximation relative to a certain value such that an amount of variability exists that is reflected, for example, in an error or deviation that provides a range about that certain value where the limits of the range are 10% less than the certain value, including the certain value and 10% greater than the certain value. Hence, as used herein, by reciting about 50, it is understood that the value can range from 45 to 55. Synonymous terms include, "essentially," and "substantially."

"Scalable," or grammatic forms thereof, is a method practiced at a bench or a laboratory scale that can be translated to a larger scale or presentation, such as, those, for example, practiced for commercial manufacturing of foods, drinks, consumer products, industrial chemicals and so on, where reaction vessels can have a volume in the hundreds or thousands of liters. Hence, in the context of the instant invention, insect cell cultures can be practiced at the 10's of, 100's of or 1000's of liter volumes, amounts, reactions and so on, or greater.

"Wild-type," or grammatic forms thereof, relates to a naturally occurring arbovirus which generally is the most common or prevalent form, trait, gene, protein, phenotype and so on in a population. In embodiments, a synonym is a, "type," or a, "reference," arbovirus. A population trait may be determined by more than one allele of a single locus or by polygenes. Hence, as the alleles or polygenes yield the same trait or substantially the same trait, the alleles or the set of polygenes are considered herein as equivalent. A wildtype arbovirus does not comprise a dysfunctional furin site resulting in enhanced furin cleavage as present in an altered arbovirus of interest. In embodiments, comparisons are made herein to demonstrate properties of a modified arbovirus of interest relative to a normal or wild type arbovirus that does not comprise a dysfunctional furin cleavage site of interest. In embodiments, an arbovirus of interest has a property that is normal or about the same as that property in a reference arbovirus, such as, growth in insect cells. For example, in embodiments, a reference DV is the serotype 2, New Guinea strain available from the ATCC (accession number VR-1584). Hence, reference herein to DV prM and amino acid numbering thereof can be relative to prM of VR-1584: or to prM and the amino acid numbering thereof of the wild type form of the mutant DV. In embodiments, a reference ZV is available from the ATCC under accession number VR-1838. Hence, reference herein to ZV prM and amino acid numbers thereof can be relative to prM of VR-1838: or to the and that of the wild type form of the mutant ZV. An arbovirus of interest, as with wild type arbovirus, propagates in insect cells. However, as to numbering of amino acids herein, because of inherent population variation, polymorphism or variability in a population, numbering in one strain, line, species and so on may not correspond directly with numbering in another strain, line species and so on. Hence, the numbering herein is not absolute as to location of any one polypeptide, cleavage site and so on, as numbering can vary even within a line, strain, species and so on because of naturally occurring variation. Therefore, numbering used herein is relative to a particular cell, virus and so on and should not be construed to be absolutely representative of all arboviruses with the same numbering in all arboviruses as that presented herein. Instead, various features provide landmarks for identifying sites and enabling an artisan to practice the claimed subject matter with any arbovirus as a design choice. For example, the furin consensus tetrapeptide at the juncture of pr and M, the downstream or carboxy terminus of pr, the upstream or amino terminus of M are landmarks that can be used to orient manipulation and alteration of the proteins. Hence, in an embodiment, numbering takes into account the numbers of the amino acids of the tetrapeptide to determine whether variability in the size of pr and of M exists, and if so, an adjustment or correlation between what is taught herein and what is being used by an artisan in a different arbovirus is made to provide the proper frame of reference.

The, "prM," protein or polypeptide of DV is 166 amino acids in length in serotypes 1-4 of DV and is cleaved after amino acid 91 by furin to yield the pr polypeptide and the M protein. The wild type prM amino acid sequence of the NGC strain of DV2 is: FHLTTRNGEP HMIVSRQEKG KSLLFKTEDG VNMCTLMAMD LGELCEDTIT YNCPLLRQNE PEDIDCWCNS TSTWVTYGTC TTTGEHRREK RSVALVPHVG MGLETRTETW MSSEGAWKHA QRIETWILRH PGFTIMAAIL AYTIGTTYFQ RVLIFILLTA VAPSMT (SEQ ID NO:8). As known, natural variation can find a wild type strain to have one or more amino acid changes from the sequence provided in SEQ ID NO:8, without disruption or enhancement of prM cleavage by furin, and without diminished propagation in mammal cells. An altered SEQ ID NO:8 of interest is one which presents with enhanced furin cleavage; and propagation of virus in insect cells but little or no propagation of that virus in mammal cells.

The, "prM," protein or polypeptide of ZV is 168 amino acids in length and is cleaved after amino acid 93 by furin to yield the pr polypeptide and the M protein. The wild type prM amino acid sequence is AEITRRGSAY YMYLDRSDAG KAISFATTLG VNKCHVQIMD LGHMCDATMS YECPMLDEGV EPDDVDCWCN TTSTWVVYGT CHHKKGEARR SRRAVTLPSH STRKLQTRSQ TWLESREYTK HLIKVENWIF RNPGFALVAV AIAWLLGSST SQKVIYLVMI LLIAPAYS (SEQ ID NO:9). As known, natural variation can find a wild type strain to have one or more amino acid changes from the sequence provided in SEQ ID NO:9, without disruption or enhancement of prM cleavage by furin, and without diminished propagation in mammal cells. An altered SEQ ID NO:9 of interest is one which presents with enhanced furin cleavage; and propagation of virus in insect cells but no propagation of that virus in mammal cells.

As used herein, "furin cleavage site," "furin recognition site," and "furin recognition and cleavage site," are interchangeable and equivalent as it is known, that generally, furin recognizes a consensus tetrapeptide of Arg-X-Lys/Arg-Arg (SEQ ID NO:16), where X is any amino acid (also sequences upstream and/or downstream of that tetrapeptide can comprise a furin cleavage site) and cleaves the peptide bond downstream of or on the carboxy terminus side of the tetrapeptide. Generally, in arboviruses, a furin cleavage site is present at the juncture of two polypeptides in a precursor polyprotein, such as, prM and precursor E2 (prE2). In some arboviruses, a furin cleavage site occurs at the juncture of pr and M. In other arboviruses with a different genomic organization and do not contain a prM, for example, some alphaviruses, a furin cleavage site occurs at the juncture of E3 and E2.

As used herein, "X logs or lower," "X logs or less," or "X logs or fewer," where X is a rational number, relates to the logarithmic scale for describing number of virus particles. As known, the scale is non-linear and is based on order of magnitude with a base of 10. The log scale finds use when there is a large range of values of a parameter. Hence, 4 logs reflects a difference between two values of $10^4$, that is one value is 10,000 units lesser or greater than the other value, 5 logs reflects a difference between two values of $10^5$, that is one value is 100,000 units lesser or greater than the other value and so on. By, "lower," "less," or "fewer," the phrase comprising those words relates to an amount that is lower in value, fewer in number and so on, or in the context herein, a smaller number of virus particles. Hence, "4 logs or lower," means the difference between two values is $10^4$, $10^{4.5}$, $10^5$ and so on, which means the number of virus particles produced in one sample is 10,000 fewer, about 31,600 fewer or about 100,000 fewer than the other sample, and in the context herein, means one sample contains 10,000 fewer virus particles than the other sample.

A focus of the instant invention is to manipulate the arbovirus genome to produce mammal cell-specific, growth-defective arbovirus where mammal cells infected with such an arbovirus do not release mature progeny virus, but continue to express arbovirus epitopes and determinants that can be recognized by the mammal host, such as, determinants expressed by, for example, M and E proteins. Cellular and/or humoral responses to an arbovirus can be generated in the mammal host. The arbovirus of interest essentially resembles wild-type virus and thus presents to the mammal host immune system the universe of arbovirus epitopes that can be found in an arbovirus, in a wildtype arbovirus. An arbovirus of interest simply cannot replicate in a host mammal cell, and hence, cannot contribute to infection of other host mammal cells and to pathology or disease in the host.

Hence, the instant invention relates to defective or dysfunctional arbovirus that comprises and expresses a majority of, if not all, the structural proteins, or at the least, the majority of the polypeptides that comprise determinants or epitopes of antibodies or immune cells generated by an infected host to an arbovirus. Thus, for example, for a flavivirus, it is preferable that most of pr, M and/or E proteins are expressed thereby as those comprise immunogenic sites of a wild-type virus. The C protein can be less of a target for the host immune system, but can be present.

All known arboviruses require furin cleavage of a precursor polyprotein for proper virus maturation and release from a host cell, such as, cleavage of prE2 into E3 and E2 in some alphaviruses, and cleavage of prM into pr and M in some flaviviruses, for proper virus maturation and eventual release of progeny virus from an infected cell.

A mutant arbovirus of interest comprises an altered or dysfunctional furin cleavage site, for example, at prE2 or at prM and optionally, alterations upstream and/or downstream from the furin consensus cleavage site resulting in enhanced cleavage by furin of, for example, prE2 or prM producing a virus that continues to replicate in insect cells but no longer replicates or replicates very poorly in mammal (which, of course, includes human) cells. Hence, alteration at and/or about a, for example, prE2 or prM furin cleavage site in an arbovirus yields a growth-restricted virus that continues to grow in insect cells but no longer grows or grows poorly in human or mammal cells, where growth indicates progeny virus is released by the infected cell.

In general, during maturation of an incipient flavivirus particle in the Golgi apparatus, immature particles present spikes comprising trimers of prM and E proteins, which, during passage through the Golgi, possibly due to a change of pH, are rearranged to form a smooth surface on the particle. That rearrangement or transformation of the spikes exposes the furin cleavage site of prM. prM is cleaved by furin and some of the pr fragments, perhaps based on pH in the Golgi, remain associated with the particle. The pr fragment is believed to prevent membrane fusion. When the incipient particle is released from the Golgi into the extracellular milieu, pr is released from the incipient particle to form the mature particle which can fuse with the cell membrane for release from the cell. Some developing particles may not mature. Nevertheless, viral protein is associated with intracellular membranes and can be destined for incorporation into the cell membrane where the viral proteins are expressed at the cell surface. Virus particles and components can be released into the milieu on cell death and lysis.

While not wanting to be bound by theory, a mutant viral genome of interest comprising an altered furin cleavage site in prM enabling enhanced cleavage of prM may entice prM to be cleaved before the developing viral particle enters the Golgi apparatus, possibly under different pH conditions, resulting in pr not being associated with the particle surface as the particle enters and resides in the Golgi. Hence, without pr to prevent membrane fusion, the virus particle is precluded from maturing properly while passing through the Golgi and is trapped within the Golgi. By prM being cleaved prematurely before entry into the Golgi, the arbovirus particle of interest does not contain pr and thus cannot be processed properly in the Golgi with the result that the virus particle binds to, fuses to and is not released from the Golgi membranes and hence, cannot be released from the cell.

However, that process is not altered in insect cells where the timing and/or efficacy of furin cleavage of, for example, prE2 or prM, is not relevant or preclusive of proper arbovirus particle maturation and release from the host insect cell. Thus, infected insect cells produce progeny arbovirus at levels comparable to, the same as or greater than found in insect cells infected with wildtype virus.

The furin consensus tetrapeptide (R-X-K/R-R (SEQ ID NO:16)) of an arbovirus of interest is located, for example, at the juncture of E3 and E2, and at the juncture of the pr polypeptide and M protein. Amino acids of the tetrapeptide are altered by amino acid substitution, site directed mutagenesis of the nucleic acid encoding that amino acid and so on, practicing known methods, such as, constructing the tetrapeptide to contain, for example, Arg as the second or X site. The altered furin site is placed into, for example, a full length nucleic acid by, for example, homologous recombination practicing known methods. Nucleic acid manipulation can be made to a cDNA which then is transcribed to form the viral RNA comprising an altered furin cleavage coding sequence as taught herein and practicing methods known in the art. Viral nucleic acids can be packaged into particles, for example, by electroporation of the viral RNA into suitable host cells. The transfected cells are cultivated, monitored for virus particle production and virus particles carrying the RNA comprising the altered furin cleavage site coding region are obtained. The DNA's, RNA's, vectors, host cells and the like are known, and some reagents are available commercially, also, see, for example, Polo et al., Zeng et al., Khromykh et al. J Virol 75(10)4633-4640, 2001: Gehrke et al., J Virol 77(6)8924-8933, 2003; and Shustov et al., J Virol 81(21)11737-11748, 2007. Virus particles then are used to infect suitable cells and cultured as known in the art. Production of progeny virus is monitored using methods taught herein to determine whether an alteration impacts virus replication in mammal cells, but not in insect cells, and to what extent propagation in the two types of cells is altered.

The instant invention relates, in part, to Flaviviruses, some of which comprise a prM polyprotein.

In embodiments, the instant invention relates to DV (such as, any one of serotypes 1-5).

The DV genome consists of a single linear, single-stranded, +sense RNA. The total genome can range from 10 to 11 kbs. There is no 3' polyadenylation. The 5' end has a methylated cap. The DV genome does not contain internal ribosomal entry sites (IRES) that provide a site of translation initiation for host ribosomes. Instead, DV employs ribosomal scanning to commence protein synthesis.

Dengue virions are spheres, 40-65 nm in diameter. Under the lipid envelope is an icosahedral capsid coat approximately 25-30 nm in diameter.

Dengue fever is an acute infectious disease characterized by biphasic fever, headache, pain in various parts of the body, prostration, rash, lymphadenopathy and leucopenia (Holstead, 1980, Immunological parameters of togavirus disease syndromes, p. 107-173, in Schlesinger (ed.), "The Togaviruses," Academic Press, Inc., NY; and Sabin, 1959, Dengue, p. 361-373, in Rivers & Horsfall (eds.), "Viral and Rickettsial Infections of Man," JB Lippincott Co., Philadelphia). DV is transported by mosquitoes. Infection with one dengue serotype can provide lifelong immunity to that subtype, but no cross-protective immunity to other serotypes.

Dengue hemorrhagic fever (DHF) is a severe febrile disease characterized by abnormalities of hemostasis and increased vascular permeability, which in some instances results in a hypovolemic shock syndrome, dengue shock syndrome (DSS) (WHO: 1975. Technical Guides for Diagnosis, Treatment, Surveillance, Prevention and Control of Dengue Hemorrhagic Fever, Geneva, CH). The mechanism of DHF/DSS may vary in different cases. The major factors contributing to DHF/DSS may include viral virulence, patient health status and secondary infection of different serotype DV.

Currently, there are five serotypes of DV, 1, 2, 3, 4 and 5. Immunity to one serotype generally does not confer immunity to another serotype.

Confoundingly, humans do not always react equally to individual serotypes. Thus, a person infected simultaneously with at least two serotypes of DV likely will mount an immune response only against one serotype. Moreover, subsequent infections, generally of a serotype different from that of the primary or previous infection, but also when the first or prior infection is benign, mild or asymptomatic, can result in more severe disease and pathology.

Reasons for the serotype dominance, selectivity or interference are unknown. It may be that in situ, virus replication, growth, maturation and release from a host cell, or antigen presentation may direct a host immune response to a particular serotype.

In any event, the less than predictable host response, serotype interference and asymptomatic infections provide numerous hurdles in developing an effective polyvalent vaccine.

Current polyvalent live vaccines are incompetent in generating equivalent immunity to all serotypes, even when the relative amounts of each serotype in the vaccine are varied in an attempt to compensate for skewed immune responses.

In practice of the subject matter of interest, various DV genomes were constructed with different amino acid substitutions at the Glu residue of the prM furin cleavage site; upstream of the consensus tetrapeptide, for example, in the 8 amino acid upstream stretch adjacent to the consensus, that is, amino acids 88-91; downstream of the consensus tetrapeptide, for example, in the 39 amino acid downstream stretch adjacent to the consensus of amino acids 88-91, that is, amino acids 92-130 (that is, within amino acids 80-130, inclusive, of prM) or combination thereof. The amino acid change(s) enhance furin cleavage of prM. When introduced into mammal host cells, replication occurred and expression occurred with production of virus particles. However, mature particles destined for movement out of the host cell were not obtained. Thus, a particle of interest infects a mammal cell once, the mutant viral genome is replicated and expressed in a mammal host cell, but mature progeny virus particles are not released by the infected host mammal or human cells.

In embodiments, the DV furin tetrapeptide cleavage site in the prM protein, $NH_2$-(88)Arg-Glu-Lys-Arg-COOH (SEQ ID NO:1), where cleavage occurs downstream from the Lys-Arg residues, is altered at the Glu site to enhance furin cleavage.

In embodiments, Glu is replaced by any amino acid. The replacement amino acid can be a non-acidic, non-neutral amino acid, such as, Gln, Asn, Gly, Lys, Arg, His, Thr, Ser, Tyr, Met or Cys. In embodiments, the replacement amino acid does not contain sulfur. Hence, the replacement amino acid is a non-acidic, non-neutral amino acid other than Met or Cys. In embodiments, the replacement amino acid does not contain an R hydroxyl group. Hence, in embodiments, the replacement amino acid is not Tyr, Ser or Thr. In embodiments, the replacement mutant amino acid is a basic amino acid. In embodiments, the replacement amino acid is Lys, Arg or His. In embodiments, the replacement amino acid is Arg.

In embodiments, an amino acid upstream of the tetrapeptide consensus is altered. For example, an amino acid in the eight amino acid stretch immediately upstream of the consensus (or the amino terminal side) of the furin cleavage site is altered to enhance furin cleavage of prM ("an altered upstream site"). Thus, alteration can occur at amino acids 80-87 of the prM polypeptide.

In embodiments, an amino acid downstream of the tetrapeptide consensus is altered. For example, an amino acid in the thirty-nine amino acid stretch immediately downstream of the consensus (or the carboxy terminal side) of the furin cleavage site is altered to enhance furin cleavage of prM ("an altered downstream site"). The alteration can occur at amino acids 92-130 of the M polypeptide.

A DV of interest comprises at least one of: (1) an altered furin tetrapeptide cleavage site: (2) an altered upstream site; and (3) an altered downstream site. A DV of interest can include a combination of any two of (1), (2) and (3). A DV of interest can comprise all three alterations.

In embodiments, the arbovirus is a ZV, which comprises a prM polyprotein.

The ZV genome consists of a single, single-stranded, positive sense RNA of 10,794 bases (although some isolates are of a different size [for example, Baronti et al., Genome Announc 2(3)1-2, 2014]). Aside from structural and nonstructural genes, there are 3' and 5' noncoding termini.

Minor levels of polymorphism exist in ZV. For example, at least two subtypes are recognized, an African lineage of virus and an Asian/South American lineage of virus. The two lineages can be distinguished serologically, that is, there is variation likely in the envelope proteins.

Symptoms of Zika fever may include fever, red eyes, joint pain, headache and a maculopapular rash, and generally lasts less than seven days. While the initial infection is not thought to be fatal for normal adults, infection during pregnancy can cause malformations and anomalies in the developing embryo and/or fetus, such as, microcephaly. Infections in adults have been linked to Guillain-Barré syndrome.

ZV is primarily mosquito-borne. Following a large outbreak of Zika in Brazil in 2015, ZV has spread through Latin America and the Caribbean, and now, into the United States.

The ZV life cycle starts with virion attachment to the surface of a host cell and subsequent entry of the cell by receptor-mediated endocytosis. As presently understood, acidification of the endosomal vesicle triggers conformational changes in the virion, fusion of the viral and cell membranes, and particle disassembly. Once the genome is released into the cytoplasm, the positive-sense RNA is translated into a single polyprotein that is processed by viral and host proteases into 10 gene products: the three structural proteins, core protein (C), premembrane protein (prM) and envelope protein (E), and seven nonstructural (NS) proteins, NS1, NS2A, NS2B, NS3, NS4A, NS4B and NS5.

The furin cleavage site of ZV is located after amino acid 93 of prM. In embodiments, the prM protein sequence upstream of and including the furin tetrapeptide cleavage site, His-His-Lys-Lys-Gly-Glu-Ala-Arg-Arg-Ser-Arg-Arg/ (SEQ ID NO:2), where cleavage occurs after the terminal Arg and is denoted with the slash, where the serine residue is replaced by Arg (of the tetrapeptide site, Arg-Ser-Arg-Arg (SEQ ID NO:10)) to provide a sequence of five arginine residues to enhance furin cleavage. In addition, the glutamic acid residue of the upstream stretch can be altered to, for example, histidine, to enhance furin cleavage. Other alterations of residues in the upstream stretch enhance furin cleavage. Alternations downstream of the tetrapeptide enhance furin cleavage. For example, alterations can be to any or all of the 26 amino acid stretch downstream of the tetrapeptide enhance furin cleavage.

The enhanced furin activity is obtained by one or more of: (1) an alteration to one or more amino acids upstream of the furin cleavage site, for example, the eight residue sequence beginning at amino acid residue 82 from the N-terminus of the prM polypeptide of ZV (i.e. amino acid residues 82-89 of prM): (2) alteration in the furin cleavage site; and (3) an alteration in one or more amino acid residues downstream (from amino acid 94 and downward) of the furin cleavage site, for example, the 26 residue sequence downstream from the furin cleavage site. Any combination of (1), (2) and (3) can be present.

For Yellow Fever virus, California encephalitis virus, Rift Valley fever virus, Tick-borne encephalitis virus, West Nile virus, Equine Encephalosis virus, Colorado Tick Fever virus, Chikungunya virus, African Swine Fever virus and other arboviruses, the furin consensus tetrapeptide recognition site is located based on the known consensus furin recognition sequence, and amino acid substitutions are made thereto to identify mutants that no longer propagate or propagate poorly in mammal cells. Amino acid alterations, such as, substitution, insertion, deletion, chemical modification and so on can be made upstream and/or downstream of the furin consensus cleavage site as well.

The making, growing and maintenance of virus in cell lines and in animals is known. Making arbovirus mutants by altering coding sequences using molecular techniques is known. Various tests for determining growth of virus in cells, production of progeny virus from cells and other assays used in the practice of the instant invention are known and the selection thereof is/are a design choice.

Another goal of the instant invention is to develop a scalable system for producing an immunogenic arbovirus of interest composition. That goal was achieved by producing arbovirus of interest that expresses the dysfunctional furin cleavage site that is cleaved at enhanced levels by furin, in insect cell lines, such as, arthropod cell lines, such as, tick or mosquito cell lines, where materials and methods for large scale production of virus by insect cells are known and available. Arthropod cell lines are available commercially, such as, silkworm cell lines and mosquito cell lines.

An arbovirus of interest grows without impediment in insect cells. Thus, an arbovirus of interest carrying a dysfunctional furin cleavage site grows, replicates, matures and can be released by the host insect cell into the environment at about the same extent or at the same level as does a wild-type arbovirus. Thus, an arbovirus of interest can produce progeny virus to the same extent or at greater levels than does an arbovirus that does not comprise a dysfunctional furin cleavage site of interest in insect cells.

The degree of progeny virus production (or propagation) can be assessed, for example, in a plaque assay or a hemagglutinin assay, as known in the art and as taught herein. A facile and sensitive method for assessing virus production is counting fluorescently labeled cells in a flow cytometer, as described in Drayman & Oppenheim, "Rapid Titration of Viruses by Flow Cytometry," Curr Prot Cell Biol 26.11.1-26.11.7, 2011. Hence, serially diluted infected cells are harvested, with detaching if needed, the cells are collected, fixed and exposed to one or more antibody reagents with at least one Ab directed to a virus protein and with at least one Ab fluorescently labeled, and then, for example, at least about 10,000 cells are read by a flow cytometer to reveal the number of fluorescently labelled cells expressing that virus protein. Thus, an arbovirus of interest can produce about the same level or amount or more progeny virus as compared to the amount of progeny virus produced by cells infected with a reference arbovirus (such as, for DV, serotype 2, New Guinea strain, ATCC No. VR-1584) in C6/36 cells (ATCC accession No. CRL-1660) or by a wild-type virus of the same strain or line not comprising a mutant virus of interest comprising an enhanced furin activity or exhibiting enhanced furin cleavage or prM.

An arbovirus of interest does not mature properly in mammal cells and particles are not released by a host mammal cell (or does not propagate) but instead immature particles are trapped within and accumulate in the host mammal cell. Thus, an arbovirus of interest produces little to no progeny virus in human or mammal cells. An arbovirus of interest produces fewer progeny virus as compared to a wildtype arbovirus, for example, 4 logs or fewer, 5 logs or fewer, 6 logs or fewer, 7 logs or fewer, 8 logs or fewer, 9 logs or fewer or no progeny as compared to the amount of progeny generated, for example, when using HT1080 cells (ATCC accession No. CCL-121).

A mutant virus of interest that does not propagate in mammal cells is desirable as disease or pathology is minimized or avoided. However, very low to no release of progeny virus is not essential or necessary. A dysfunctional virus that when infected in a mammal cell that produces, for example, 4 logs or less, 5 logs or less, 6 logs or less, or less progeny virus as compared to a like cell infected with a wild type virus can be used an immunogen despite release of low or small amounts of progeny virus because the host immune system ultimately will clear virus and cells expressing a virus antigen.

Virus comprising an altered and dysfunctional furin site of interest is infectious, but cannot or does not produce infectious, progeny virions from the infection of mammal cells. Thus, a non-replicating particle is one that infects a host mammal cell, such as, a human cell, but that host cell does not yield or release progeny virus particles resulting from that infection. But, that infected mammal host cell expresses arbovirus epitopes in and on an infected cell.

The unique character of the defective virus of interest provides a source for effective and safe arbovirus immunogenic compositions, and large amount of virus can be obtained cost effectively by growing virus of interest in insect cells. A dysfunctional virus of interest can produce about the same amount of progeny virus as does a reference virus, when infected into the same type of insect cell. In embodiments, a dysfunctional virus of interest produces more virus from an insect cell than does a reference virus infected into that insect cell type. In embodiments, a dysfunctional virus of interest produces less virus than does a reference virus. A highly immunogenic dysfunctional viral strain mimics the process of natural infection of arbovirus and enables the mammal host to generate and to produce a long-lasting and broad arbovirus immunity without or with minimal pathology. Thus, an altered arbovirus of interest is one that contains the genetic material to express as many or all of the epitopes expressed by wild-type prM, M and E proteins, and perhaps, C as well, of a wildtype arbovirus.

An arbovirus of interest can infect many, if not all susceptible cells following appropriate titration. The degree of infectivity can be assessed using a standard and known assay. For example, Vero cells in a six-well dish are infected with arbovirus at serial dilution and the cells are agitated in a rocker platform at 37° ° C. Cell culture fluid is collected at 48 hours. The number of virus released into the culture medium can be determined practicing known methods, such as, those taught herein.

To prepare partially purified arbovirus particles, for example, culture fluid is clarified by, for example, centrifugation at 16,000×g in a microcentrifuge for 15 min at 4°C, and the particles are pelleted from the supernatant fluid by ultracentrifugation at 40,000 rpm for 2 hours at 4° C. in an AH650 rotor of a Sorvall OTD55B centrifuge. The pellets are resuspended in 50 µl of phosphate-buffered saline (PBS) and left to dissolve overnight at 4° C.

To determine the titer of the arbovirus, for example, baby hamster kidney (BHK)-21 cells on eight-well chamber slides are infected with 50 µl of serial 10-fold dilutions of cell culture fluid or of resuspended pelleted material for 2 hours at 37°C. The fluid then is replaced with 1 ml of Dulbecco's minimal essential medium supplemented with 2% fetal bovine serum. Cells are incubated for 24 hours at 37° C. in a $CO_2$ incubator and then are subjected to immunofluorescence (IF) analysis with an arbovirus-specific Ab or mAb (commercially available or made as known in the art), an HMAF as described below or a polyclonal antiserum with the requisite specificity, a reagent that forms a sandwich with the virus-specific reagent which carries a detectable reporter, and using appropriate controls.

The titers of virus (in infectious units (IU) per milliliter) present in harvested culture fluids (CF's) also were determined by infection of, for example, rhesus kidney epithelial cells (for example, LLC-MK2 (ATCC) cells) followed by indirect immunofluorescence analysis (IF) with arbovirus-specific reagents and labelling reagents, for example, hyperimmune mouse ascitic fluid (HMAF) comprising an mAb.

Both humoral antibody and cellular immune responses are implicated in protection and recovery from DV infection. The arbovirus of interest induces both arms of the immune response. The particles are composed of prM, M and/or E proteins and thus, the particles of interest are broad based immunogens and simulate infection with wildtype virus. But the particles of interest infect mammal host cells, and in those cells, additional prM, M and/or E protein is expressed at or by the host cell. The prM, M and/or E proteins either can be released from those cells, providing additional antigenic stimuli to the host, or can be expressed at the infected host cell surface to provide yet another mode of antigenic stimulus to the host. An arbovirus of interest optionally can express nonstructural proteins, such as, NS1. Previous reports demonstrated that those NS viral proteins can induce a protective immune response (Heinz & Roehrig, 1990, in, "Immunochemistry of Viruses, Vol II," Amsterdam-NY-Oxford, Elsevier, p. 289-305; Heinz, 1986, Adv Virus Res 31:103-168: Bray & Lai, 1991, Virol, 185:505-508; Henchal et al., 1988, J Gen Virol 69:2101-2107; and Schlesinger et al., 1986, J Virol 60:1153-1155).

Suitable models for testing the efficacy of a pharmaceutical composition of interest include animal models that simulate arbovirus infection. For example, a protocol used for immunization of mice and subsequent challenge with an arbovirus has been described (Bray et al., 1989, J Virol 63:2853-2856). Briefly, in 10 mice for each group, female BALB/c mice are immunized at 3 weeks of age (day 1) and again on day 14 by intraperitoneal (ip) inoculation of virus, such as, DV. Control animals receive phosphate-buffered saline (PBS). All animals are bled on day 0 and on day 21. In the case of DV, mice are challenged on day 22 by intracerebral injection of 100 times the 50% lethal dose ($LD_{50}$) of virus. Following challenge, mice are observed for 21 days for signs of pathology, and mice with symptoms (encephalitis, paralysis or death) are recorded daily. Sera also are collected from survivors for comparison with pre-challenge sera.

The dose of each virus is determined. The seroresponse of immunized mice to individual arbovirus proteins is analyzed by, for example, ELISA or radioimmunoprecipitation of labeled arbovirus antigens using commercially available labeling kits and antibodies. A plaque reduction assay can be used to measure titers of arbovirus-specific neutralizing antibodies in mouse sera. For example, approximately 0.5 ml of a serum sample to be used in the assay first is heat inactivated by incubation for 30 min at 56° C. Four-fold dilutions of serum in a final volume of 0.3 ml, starting at 1:10 dilution, are prepared using medium M199 with 2% heat-inactivated fetal bovine serum (FBS) as diluent. To each 0.3 ml aliquot of diluted serum is added an equal volume of medium containing 150-180 plaque-forming units (PFU) of virus. Virus and serum are mixed and incubated for 30 min at 37°C. In each assay, a no serum control and controls consisting of each arbovirus type-specific Ab, for example, at two dilutions, also are included. Virus/serum and control mixtures are plated on confluent monolayers of, for example, LLC-MK2 cells in Costar six-well plates (Corning Inc., Corning, NY) at 0.2 ml/well. Duplicate wells are infected for each sample. Virus adsorption is carried out for 1 hour at room temperature with manual rocking every 15 min. Wells then are overlaid with medium containing 1% agarose (SeaKem LE; BioWhittaker, Rockland, ME) in Earle's balanced salt solution plus 10% FBS with added essential vitamins and amino acids (Invitrogen) at 6 ml/well. Plates are incubated for 7 days at 37° C. in 5% $CO_2$. Wells then are overlaid with 4% neutral red solution (4 ml of neutral red solution added to 96 ml of PBS) containing 1% agarose. Plates are incubated for 24 hours at 37° C. The average of plaque counts is used to calculate the 50% reduction in plaque number level.

In embodiments, a virus composition of interest is one that is polyvalent, that is, bivalent, trivalent, tetravalent and so on, and is one that immunizes a host to plural arbovirus serotypes, generally, of one virus, but may comprise antigens from plural virus species, such as, comprising plural mutant viruses of interest. Interference or dominance of one serotype at the expense of one or more other serotypes is not observed. That may be because immunogenicity does not rely on virus production and on constant replication of new virus.

The arbovirus of interest is incorporated into pharmaceutical compositions suitable for administration to serve as an immunogen, as known in the immunology art. Such compositions typically comprise the active ingredient and a pharmaceutically acceptable carrier. As used herein, the language, "pharmaceutically acceptable carrier," is intended to include any and all solvents, dispersion media, coatings, antibacterial and antifungal agents, isotonic and absorption delaying agents and the like, compatible with pharmaceutical administration. The use of such media and agents for pharmaceutically active substances is known in the art and as a design choice. Except insofar as any conventional media or agent is incompatible with the active compound, use thereof in the compositions is contemplated. Supplementary pharmacologically active compounds, such as, an adjuvant, also can be incorporated into the compositions.

A pharmaceutical composition of the invention for use as disclosed herein is formulated to be compatible with the intended route of administration. Examples of routes of administration include parenteral, e.g., intravenous, intradermal, subcutaneous, transdermal (including, for example, topical), transmucosal and rectal administration.

Solutions or suspensions used for parenteral, intradermal or subcutaneous application can include the following components: a sterile diluent, such as, water for injection, saline solution, fixed oils, polyethylene glycols, glycerin, propylene glycol or other synthetic solvents; antibacterial agents, such as, benzyl alcohol or methyl parabens; antioxidants, such as, ascorbic acid or sodium bisulfite; chelating agents, such as, EDTA; buffers, such as, acetates, citrates or phosphates; and agents for the adjustment of tonicity, such as, sodium chloride or dextrose. pH can be adjusted with acids or bases, such as, HCl or NaOH. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor ELR (BASF; Parsippany, NJ) or phosphate-buffered saline (PBS). In all cases, the composition must be sterile and should be fluid to the extent that syringability exists. The composition must be stable under the conditions of manufacture and storage and must be preserved against the contaminating action of microorganisms, such as, bacteria and fungi. The carrier can be a solvent or dispersion medium containing, for example, water, ethanol, polyol (for example, glycerol, propylene glycol, liquid polyethylene glycol and the like) and suitable mixtures thereof. The proper fluidity can be maintained, for example, by use of a coating, such as, lecithin, by maintenance of the required particle size in the case of dispersion and by use of surfactants. Prevention of the action of microorganisms can be achieved by various antibacterial and antifungal agents, for example, parabens, chlorobutanol, phenol, ascorbic acid and the like. It may be preferable to include isotonic agents, for example, sugars, polyalcohols, such as, mannitol and sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in a required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparing include vacuum drying and freeze drying that yield a powder of the active ingredient plus any additional desired ingredient from a previously sterile-filtered solution thereof.

Oral compositions generally include an inert diluent or an edible carrier. The composition can be enclosed in gelatin capsules or compressed into tablets, which may be coated or treated, for example, to provide an enteric composition, a delayed release formulation and so on. For the purpose of oral therapeutic administration, the active compound can be incorporated with excipients and used in the form of tablets, troches or capsules. Oral compositions also can be prepared using a fluid carrier to yield a syrup, an elixir or a liquid formulation, or for use as a mouthwash, wherein the compound in the fluid carrier is applied orally and swished and expectorated or swallowed.

Pharmaceutically compatible binding agents and/or adjuvant materials can be included as part of the composition. The tablets, pills, capsules, troches and the like can contain any of the following ingredients or compounds of a similar nature: a binder, such as, a microcrystalline cellulose, gum tragacanth or gelatin: an excipient, such as, starch or lactose: a disintegrating agent, such as, alginic acid, Primogel or corn starch: a lubricant, such as, magnesium stearate or Sterotes: a glidant, such as, colloidal silicon dioxide: a sweetening agent, such as, sucrose or saccharin: or a flavoring agent, such as, peppermint, methyl salicylate or orange flavoring. The particles of interest can be encapsulated into forms that will survive passage through the gastric environment. Such forms are commonly known as enteric-coated formulations.

For administration by inhalation, the compound can be delivered in the form of, for example, an aerosol spray from a pressurized container or dispenser that contains a suitable propellant, e.g., a gas, such as, carbon dioxide or a nebulizer, or a mist. The formulation can be liquid, dry, such as, a finely divided powder, and so on.

Systemic administration also can be by a transmucosal or transdermal means. For transmucosal or transdermal administration, penetrants appropriate to the barrier to be permeated are used in the formulation. Such penetrants generally are known in the art and include, for example, for transmucosal administration, detergents, bile salts and fusidic acid derivatives. Transmucosal administration can be accomplished through the use of nasal sprays or enemas. For transdermal administration, the active compounds can be formulated into ointments, salves, foams, gels or creams as generally known in the art. The composition can be delivered using a patch applied to skin.

When in the form of suppositories with a composition of interest can comprise a conventional suppository base, such as, cocoa butter and other glycerides.

In embodiments, the active compound is prepared with carriers that protect the compound against rapid elimination from the body, such as in a controlled release formulation, including implants and microencapsulated delivery systems. Biodegradable, biocompatible polymers can be used, such as, ethylene vinyl acetate, polyanhydrides, polyglycolic acid, collagen, polyorthoesters and polylactic acid.

Methods for preparation of such formulations will be apparent to those skilled in the art. The materials can be obtained from commercial sources, such as, Johnson & Johnson and Encapsula Nano Sciences (Brentwood, TN).

Liposomal suspensions (including liposomes targeted with monoclonal antibodies and other such targeting molecules) also can be used as pharmaceutically acceptable carriers. Those can be prepared according to methods known to those skilled in the art, for example, as described in U.S. Pat. No. 4,522,811.

It can be advantageous to formulate oral or parenteral compositions in unit dosage form for ease of administration and uniformity of dosage. "Unit dosage form," as used herein refers to physically discrete units suited as unitary dosages for a subject to be treated; each unit containing a predetermined quantity of active compound calculated to produce the desired therapeutic effect in association with the required pharmaceutical carrier.

The pharmaceutical compositions can be included in a container, pack, kit or dispenser together with instructions for administration.

Another method of administration comprises addition of a compound of interest into or with a food or drink, as a food supplement or additive, or as a dosage form taken on a prophylactic basis, similar to a vitamin.

The dosages, for example, preferred route of administration and amounts, are obtainable based on empiric data obtained from preclinical and clinical studies, practicing methods known in the art. For repeated administrations over several days or longer, depending on the condition, the treatment is sustained until a desired suppression of disease symptoms occurs. However, other dosage regimens may be useful. The progress of therapy is monitored by conventional techniques and assays. An exemplary dosing regimen is disclosed in WO 94/04188. The specification for the dosage unit forms of the invention is dictated by and can be directly dependent on the unique characteristics of the active compound and the particular therapeutic effect to be achieved and the limitations inherent in the art of compounding such an active compound for the treatment of individuals. Hence, the number of virus particles administered to an adult human can be extrapolated from therapeutic amounts delivered to model animals, such as, mice, rats, monkeys and so on. For example, based on mouse studies, from about $10^6$ particles (or IU), from about $10^7$ particles, from about $10^8$ particles, from about $10^9$ particles or more can be administered per dose or in divided doses. Amounts or doses can be adjusted as empiric data become available, as known in the art.

A virus of interest can be used to generate an effective immune response in an individual, where effective comprises minimizing, reducing or preventing symptoms or pathology in the individual. Because host immune response is determinative in obtaining a therapeutic response, which may be graded in any one individual, as with any drug, a virus or interest may or may not be therapeutic and may or may not yield the desired response from a virus recipient. Dosing, virus presentation route and means, use of an adjuvant and other immunology factors may resolve lack of or a tepid host immune response in an individual.

That phenomenon is manifest at the population level as well as not every recipient in a population of a virus of interest will mount a therapeutic immune response and the number of responders in any one population may vary from that of another population.

Utility of a dysfunctional virus of interest is not conditioned on a larger percentage of responders in a population, a higher level of immunoprotection in a population, commercial viability, commercial success and so on, but only if in one individual, a dysfunctional virus of interest generates a therapeutic immune response that reduces or prevents symptoms or disease.

The invention now will be exemplified in the following non-limiting examples.

Example 1

The DV virion is composed of 6% RNA, 66% protein, 9% carbohydrate and 17% lipid (Russell et al., Chemical and Antigenic Structure of Flaviviruses, in, Schlesinger eds., "The Togaviruses: Biology, Structure, Replication," New York, Academic, 1980, p. 503-529; and Trent & Naeve, Biochemistry and Replication, in Monath, ed., "St. Louis Encephalitis," Washington, DC, American Public Health Association, 1980, p. 159-199). An electron-dense nucleocapsid is composed of C (capsid) protein and genomic RNA. The envelope protein, E, and membrane (M) protein are embedded in the lipid bilayer by C-terminal hydrophobic anchors. However, immature particles found within intracellular vesicles contain exclusively unprocessed pre-M (prM) and are less infectious than released virions (Morens, Clin Infect Dis, 1994, 19:500-512).

The genome of DV is uniform, and is a single-stranded, positive-sense RNA molecule of about 10-11 kb, containing a single ORF constituting roughly 95% of the genome (Chambers et al., Ann Rev Microbiol, 1990, 44:649-688). Full length genomic RNA's appear to be the only virus-specific messenger RNA (mRNA) molecules in DV-infected cells. On infection, the viral RNA is translated into a polyprotein of about 3400 amino acids that is processed into 10 gene products: the three structural proteins, C, prM and E; and seven nonstructural (NS) proteins, 1, 2A, 2B, 3, 4A, 4B and 5 (Bhamarapravati & Yokan, Live attenuated tetravalent vaccine, in Gubler & Kuno, eds., "Dengue and Dengue Hemorrhagic Fever," Wallingford, CAB International, 1997, pp 367-377; and Falgout & Markoff, 1995, The family flaviviridae and its diseases, p. 47-66, in, Porterfield, ed., "Exotic Viral Infections," Chapman and Hall Medical, London, United Kingdom).

Example 2

Mutant DV's were generated from a full-length infectious cDNA clone of DV2 New Guinea C strain (ATCC No. VR-1584). The mutant DNA fragments were created by PCR and introduced into a full-length clone by homologous recombination as described (Zeng et al., J Virol. 1998 September;72(9):7510-22). The mutations were confirmed by DNA sequencing. Mutant DV RNA's were synthesized by in vitro transcription as described by Polo et al., J Virol. 1997;71(7):5366-74.

Growth kinetics of the mutant DV's showed a difference of virus growth between infected Vero cells (ATCC CCL-81) (human) and infected C6/36 cells (CRL-1660) (mosquito). Wild type DV2 (DENV2) prM (SEQ ID NO:3) and four mutants, where Glu (E of DENV2) of the furin recognition site was replaced by Arg (R) (D2-89R, SEQ ID NO:4), Val (V) (D2-89V, SEQ ID NO:5), Ser (S) (D2-89S, SEQ ID NO:6) or Gly (G) (D2-89G), SEQ ID NO:7), were tested for growth in human Vero cells and in mosquito C6/36 cells.

The D2-89R mutant where Glu is replaced by R propagates in insect cells and demonstrated no replication in human cells.

Example 3

Mutants were generated with a second serotype of DV, from a full-length infectious cDNA clone of DV1, Western Pacific, 74 strain (Genbank No. U88536). The mutant DNA fragments were created by PCR and introduced into a full-length clone by homologous recombination as described (Markoff et al., J Virol. 2002:76(7): 3318-28). The mutations were confirmed by DNA sequencing. Mutant DV RNA's were synthesized by in vitro transcription as described by Polo et al.

Growth kinetics of the mutant DV's showed a difference of virus growth between infected Vero cells (ATCC CCL-81) (human) and infected C6/36 cells (CRL-1660) (mosquito).

Example 4

A DV1 mutant was made as described in Examples 2 and 3, comprising the following sequence:
CSQTGEHRRRKRSVALAPHVGL-
GLETRTETWMSSEGAWKHAQRIETWIL RH (SEQ ID NO:17).

That sequence begins at amino acid 80 of the DV1 prM polypeptide and in the consensus furin tetrapeptide, D was changed to R. Cleavage occurs between R and S in the sequence above.

Growth kinetics of the mutant DV1 showed a difference of virus growth between infected Vero cells (ATCC CCL-81) (human) and infected C6/36 cells (CRL-1660) (mosquito).

Example 5

Western blot analysis practicing a known method with a commercially available DV prM mAb and comparing band intensity and band size to infer molecular weight, demonstrated that furin cleavage efficiency of mutant DV's was increased in both Vero cells (CCL-81) and in C6/36 cells (CRL-1660).

Example 6

Growth of mutant DV's in mammal cells was investigated by indirect immunofluorescent staining. mAb 4G2 from ATCC (HB-112) was used in the method of Polo et al.

Positive fluorescence was observed from 1 day to 3 days post infection with increasing brightness and increasing numbers of positive cells for the positive controls using parent DV2 virus. On the other hand, when infected with mutant D2-89R, the intensity of and number of fluorescing cells decreased progressively over that time period. No new colonies formed from 1 to 3 days post infection.

Thus, mutant D2-89R initiated only a single round of infection in the human cells and did not produce infectious progeny virus particles.

Example 7

To verify that mutant D2-89R is growth-restricted in human cells, skin fibroblast cells (CRL-2522, ATCC) were infected in vitro with DV2 or D2-89R, and the presence of viral envelope antigens was evaluated by immunofluorescence at different times (hours) postinfection (hpi) as described herein. DV2 propagated and produced progeny virus in CRL-2522 cells whereas mutant D2-89R did not.

A gradual increase in production of viral particles over time, indicating active viral replication in the infected cells, was observed for cells infected by wildtype DV2 virus.

On the other hand, mutant D2-89R infected cells did not produce any viral progeny.

Example 8

To assess the protective efficacy of the mammal cell-specific growth restriction of the mutant DV of interest against DV challenge, groups of 6 week AG129 mice (N=6/group) received a single ip immunization of $10^5$ infectious units (IU) of mutant D2-89R. The control group mice were injected ip with 50 µl of phosphate buffered saline (PBS).

The two groups of mice did not show any visible different mobility and behavior post immunization.

Ten days post immunization, the D2-89R-injected mice and PBS control AG129 mice were injected ip with $10^5$ plaque-forming units (PFU) (which is a hundred-fold $LD_{50}$ inoculation) of DV2.

The PBS-injected control mice inoculated with DV2 developed viremia. In contrast, a single immunization with mutant D2-89R provided complete protection against DV2 challenge with no detectable viremia (<100 copies/ml) at any time point (N=10).

Moreover, all D2-89R-exposed mice were healthy throughout the experiment, whereas all mice exposed only to PBS succumbed after DV2 challenge, see FIG. 1.

Example 9

To assess the safety of DV mutants, AG129 mice were used because AG129 mice can be lethally infected by DV2 with as low as 1 PFU of virus.

A group of 6 adult AG129 received $10^6$ IU of mutant D2-89R, ip. For control groups, equal numbers of mice per group were injected ip with $10^1$, $10^2$ and $10^3$ PFU of DV2. Viral load following DV2 and D2-89R injection were quantified by RT-PCR.

The DV2 infected groups of mice developed detectable viremia and all succumbed post infection.

On the other hand, mice exposed to mutant D2-89R had no detectable viremia and all survived the length of the experiment (15 days) without any sign of sickness and change in weight.

Example 10

The ZV electron-dense nucleocapsid is composed of C (capsid) protein and genomic RNA. The envelope protein, E, and membrane (M) protein are embedded in the lipid bilayer (Russell et al., Chemical and Antigenic Structure of Flaviviruses, in Schlesinger, ed., The Togaviruses: Biology, Structure, Replication. New York: Academic: 1980:503-529; and Trent & Naeve, Biochemistry and Replication, in Monath, ed. St. Louis Encephalitis. Washington, DC: American Public Health Association: 1980 p. 159-199).

The ZV genome is a single-stranded, positive-sense RNA molecule of about 10-11 kb, containing a single ORF constituting roughly 95% of the genome (Chambers et al., Ann Rev Microbiol 1990, 44:649-688). On infection, the infectious viral RNA is translated and processed into structural proteins and nonstructural proteins (Bhamarapravati & Yokan: Live attenuated tetravalent vaccine, in Gubler & Kuno, eds., Dengue and Dengue Hemorrhagic Fever. Wallingford, CAB International, 1997, pp 367-377; and Falgout & Markoff, 1995, The family flaviviridae and its diseases, p. 47-66. in: JS Porterfield (ed.), Exotic Viral Infections. Chapman and Hall Medical, London, United Kingdom).

Example 11

A full-length infectious cDNA clone of ZV MR766 from ATCC was subjected to point mutations to produce growth restriction in mammal cells. The mutations were confirmed by DNA sequencing. Mutant ZV genomic RNA's were synthesized by in vitro transcription, and C6/36 mosquito cells were transfected with the mutant viral RNA's by TransIT®-mRNA (Mirus Bio, Madison, WI) following manufacturer's instructions. The mutant ZV's were collected 7 days post transfection. Virus growth kinetics were determined in both mammal (Vero) cells and C6/36 cells.

A point mutation was induced in the ZV genome to alter the sequence near the furin cleavage site as follows:
Wild-Type:
HHKKGEARRSRRAVTLPSHSTRKLQTRSQTWLES-REYTKHIKVENWIFRN (SEQ ID NO:11)
Mutant:
HHKKGEARRRRRAVTLPSHSTRKLQTRSQTWLES-REYTKHIKVENWIFRN (SEQ ID NO:12).

The single alteration from serine to arginine resulted in reduction of propagation in Vero cells whereas propagation in mosquito cells remained relatively unchanged from control.

Example 12

The procedure of Example 11 was followed. The same Ser to Arg substitution was used, as well as replacement of Glu (E) (between G and A) with His (H) to yield a mutant with two point mutations.

Propagation in human cells was reduced to a level less than observed with the mutant of Example 11, with no impact on replication in insect cells.

Example 13

The procedure of Example 11 was followed. The first 12 amino acids of the sequence presented in Example 11 were replaced with TTTGEHRRRKRS (SEQ ID NO:13).

Propagation in human cells was reduced to a level less than observed with the mutant of Example 11, with no impact on replication in insect cells.

Example 14

The procedure of Example 11 was followed. The first 22 amino acids of the sequence presented in Example 11 were replaced with TTTGEHRRRKRSVALVPHVGMG (SEQ ID NO:14).

Propagation in human cells was reduced to a level less than observed with the mutant of Example 11, with no impact on replication in insect cells.

Example 15

The procedure of Example 11 was followed. The first 37 amino acids of the sequence presented in Example 11 were replaced with TTTGEHRRRKRSVALVPHVGM-GLETRTETWMSSEGAW (SEQ ID NO:15) to form the ZV M2 mutant.

Propagation in human cells was reduced to a level less than observed with the mutant of Example 11, with no impact on replication in insect cells.

Example 16

To assess the protective efficacy of the mammal cell-specific growth restriction of the mutant SV of interest against SV challenge, groups of 6 week AG129 mice (N=6/group) received a single ip immunization of $10^5$ infectious units (IU) of mutant M2 of Example 15. The control mice were injected ip with 50 μl of PBS.

The two groups of mice did not show any visible different mobility and behavior post immunization.

Fourteen days post immunization, the M2-injected mice and PBS control AG129 mice were injected ip with $10^3$ plaque-forming units (PFU) (which is a hundred-fold $LD_{50}$ inoculation) of wildtype SV.

The PBS-injected control mice inoculated with SV developed viremia. In contrast, a single immunization with mutant M2 provided complete protection against SV challenge with no detectable viremia (<100 copies/ml) at any time point (N=10).

Moreover, all M2-exposed mice were healthy throughout the experiment, whereas all mice exposed only to PBS succumbed after SV challenge, see FIG. 2.

Example 17

To assess the safety of the mammal cell-specific growth restriction of the mutant SV of interest, groups of 6 week AG129 mice (N=6/group) received a single ip immunization of $10^5$ infectious units (IU) of mutant M2 or of wild type ZV.

Figure 3:
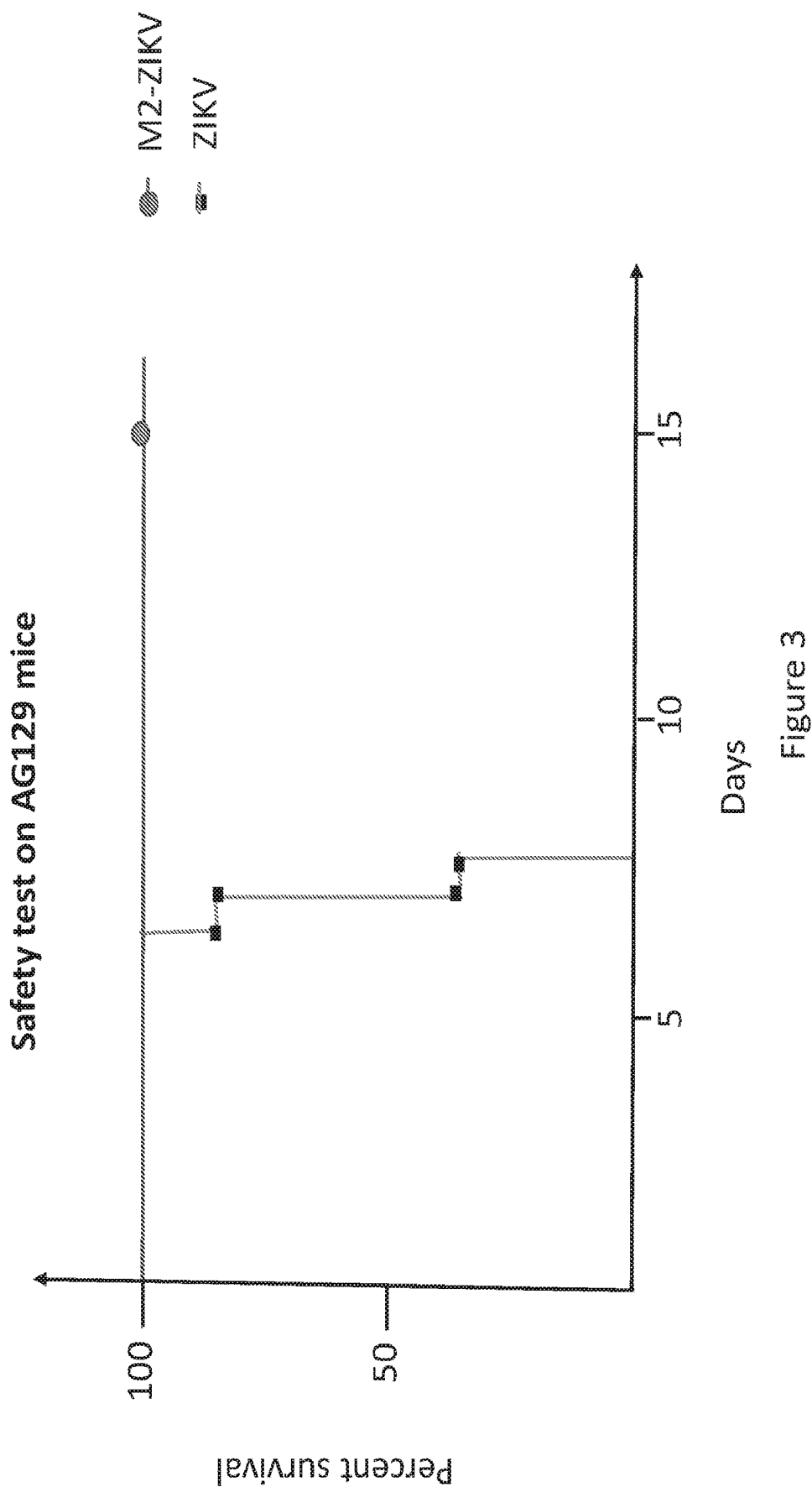
FIG. 3 depicts a safety graph comprising data obtained from mice that received either wild type SV or the SV M2 mutant.

The M2-exposed mice were healthy throughout the experiment, whereas all mice exposed only to PBS succumbed after SV challenge, see FIG. 3.

Example 18

The materials and methods of Examples 2-9 are practiced with a type strain of Yellow Fever virus.

The prM furin recognition site is located and amino acid substitutions are made thereto as provided above and as known in the art. Mutants of interest are identified as those that no longer propagate or propagate at lower levels in human cells, as provided hereinabove. Amino acid alterations, such as, substitution, insertion, deletion, chemical modification and so on are made upstream and/or downstream of the furin cleavage site as well.

A Yellow Fever virus mutant that replicates in insect cells but has lower replication success in human cells is identified.

Example 19

The materials and methods of Examples 2-9 are practiced with a type strain of California Encephalitis virus.

The prM furin recognition site is located and amino acid substitutions are made thereto as provided above and as known in the art. Mutants of interest are identified as those that no longer propagate or propagate at lower levels in human cells, as provided hereinabove. Amino acid alterations, such as, substitution, insertion, deletion, chemical modification and so on, are made upstream and/or downstream of the furin cleavage site as well.

A California Encephalitis virus mutant that replicates in insect cells but has lower replication success in human cells is identified.

Example 20

The materials and methods of Examples 2-9 are practiced with a type strain of Rift Valley fever virus.

The prM furin recognition site is located and amino acid substitutions are made thereto as provided above and as known in the art. Mutants of interest are identified as those that no longer propagate or propagate at lower levels in insertion, deletion, chemical modification and so on are made upstream and/or downstream of the furin cleavage site as well.

A Rift Valley Fever virus mutant that replicates in insect cells but has lower replication success in human cells is identified.

Example 21

The materials and methods of Examples 2-9 are practiced with a type strain of Tick-borne Encephalitis virus.

The prM furin recognition site is located and amino acid substitutions are made thereto as provided above and as known in the art. Mutants of interest are identified as those that no longer propagate or propagate at lower levels in human cells, as provided hereinabove. Amino acid alterations, such as, substitution, insertion, deletion, chemical modification and so on are made upstream and/or downstream of the furin cleavage site as well.

A Tick-borne Encephalitis virus mutant that replicates in insect cells but has lower replication success in human cells is identified.

Example 22

The materials and methods of Examples 2-9 are practiced with a type strain of West Nile virus.

The prM furin recognition site is located and amino acid substitutions are made thereto as provided above and as known in the art. Mutants of interest are identified as those that no longer propagate or propagate at lower levels in mammal cells, as provided hereinabove. Amino acid alterations, such as, substitution, insertion, deletion, chemical modification and so on are made upstream and/or downstream of the furin cleavage site as well.

A West Nile virus mutant that replicates in insect cells but has lower replication success in mammal cells is identified.

Example 23

The materials and methods of Examples 2-9 are practiced with a type strain of Equine Encephalosis virus.

The prM furin recognition site is located and amino acid substitutions are made thereto as provided above and as known in the art. Mutants of interest are identified as those that no longer propagate or propagate at lower levels in mammal cells, as provided hereinabove. Amino acid alterations, such as, substitution, insertion, deletion, chemical modification and so on are made upstream and/or downstream of the furin cleavage site as well.

An Equine Encephalosis virus mutant that replicates in insect cells but has lower replication success in mammal cells is identified.

Example 24

The materials and methods of Examples 2-9 are practiced with a type strain of Colorado Tick Fever virus.

The prM furin recognition site is located and amino acid substitutions are made thereto as provided above and as known in the art. Mutants of interest are identified as those that no longer propagate or propagate at lower levels in human cells, as provided hereinabove. Amino acid alterations, such as, substitution, insertion, deletion, chemical modification and so on are made upstream and/or downstream of the furin cleavage site as well.

A Colorado Tick Fever virus mutant that replicates in insect cells but has lower replication success in human cells is identified.

Example 25

The materials and methods of Examples 2-9 are practiced with a type strain of Chikungunya virus.

The prM furin recognition site is located and amino acid substitutions are made thereto as provided above and as known in the art. Mutants of interest are identified as those that no longer propagate or propagate at lower levels in insertion, deletion, chemical modification and so on, are made upstream and/or downstream of the furin cleavage site as well.

A Chikungunya virus mutant that replicates in insect cells but has lower replication success in human cells is identified.

Example 26

The materials and methods of Examples 2-9 are practiced with a type strain of African Swine Fever virus.

The prM furin recognition site is located and amino acid substitutions are made thereto as provided above and as known in the art. Mutants of interest are identified as those that no longer propagate or propagate at lower levels in human cells, as provided hereinabove. Amino acid alterations, such as, substitution, insertion, deletion, chemical modification and so on are made upstream and/or downstream of the furin cleavage site as well.

An African Swine Fever virus mutant that replicates in insect cells but has lower replication success in human cells is identified.

Example 27

Adult Rhesus monkeys were allocated to experimental and control groups of 4-6 animals per group. The experimental group animals received varying doses ($10^5$-$10^{10}$ IU) of mutant D2-89R of Example 2. Animals of the control group received an equivalent volume of PBS.

The animals were held for 4 weeks during which period, the animals were tested for circulating anti-Dengue antibody, viral load and cell immunofluorescence to detect presence, extent and amount of virus and host response thereto, as well as monitoring for any symptoms of Dengue infection, such as, fever and weight loss.

The animals then were challenged with wildtype DV2 and monitored for symptoms, such as, fever and weight loss, and serologic parameters, such as, viral load and Dengue antibody.

The control animals exhibit symptoms of Dengue infection whereas the monkeys that received the mutant of interest are symptom free.

Example 28

Adult Rhesus monkeys were allocated to experimental and control groups of 4-6 animals per group. The experimental group animals received varying doses ($10^5$-$10^{10}$ IU) of the DV1 mutant of Example 4. Animals of the control group received an equivalent volume of PBS.

The animals were held for 4 weeks during which period, the animals were tested for circulating anti-Dengue antibody, viral load and cell immunofluorescence to detect presence, extent and amount of virus and host response thereto, as well as monitored for any symptoms of Dengue infection, such as, fever and weight loss.

The animals then were challenged with wildtype DV1 and monitored for symptoms, such as, fever and weight loss, and serologic parameters, such as, viral load and Dengue antibody.

The control animals exhibit symptoms of Dengue infection whereas the monkeys that received the mutant of interest are symptom free.

Example 29

Adult Rhesus monkeys were allocated to two experimental and two control groups of 4-6 animals per group. The experimental group animals received varying doses ($10^5$-$10^{10}$ IU) of mutant Zika virus of Example 14. Animals of the control group received an equivalent volume of PBS.

The animals were held for 4 weeks during which period, the animals were tested for circulating anti-Zika antibody, viral load and cell immunofluorescence to detect presence, extent and amount of virus and host response thereto, as well as monitored for any symptoms of Zika infection, such as, fever, viremia, rash and weight loss.

The animals then were challenged with wildtype ZV. A pair of an experimental group and a control group were challenged with a wildtype ZV Africa strain and the other pair of an experimental group and a control group were challenged with a wildtype ZV Asia strain. The animals were monitored for symptoms, such as, fever, rash and weight loss, and serologic parameters, such as, viral load and Zika antibody.

The control animals exhibit symptoms of Zika infection whereas the monkeys that received the mutant of interest are symptom free.

Example 30

Adult Rhesus monkeys were allocated to two experimental and two control groups of 4-6 animals per group. The experimental group animals received varying doses ($10^5$-$10^{10}$ IU) of mutant Zika virus of Example 15. Animals of the control group received an equivalent volume of PBS.

The animals were held for 4 weeks during which period, the animals were tested for circulating anti-Zika antibody, viral load and cell immunofluorescence to detect presence, extent and amount of virus and host response thereto, as well as monitored for any symptoms of Zika infection, such as, fever, viremia, rash and weight loss.

The animals then were challenged with wildtype ZV. A pair of an experimental group and a control group were challenged with a wildtype ZV Africa strain and the other pair of an experimental group and a control group were challenged with a wildtype ZV Asia strain. The animals were monitored for symptoms, such as, fever, rash and weight loss, and serologic parameters, such as, viral load and Zika antibody.

The control animals exhibit symptoms of Zika infection whereas the monkeys that received the mutant of interest are symptom free.

All references cited herein are incorporated by reference in entirety herein.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

SEQUENCE LISTING

```
<160> NUMBER OF SEQ ID NOS: 17

<210> SEQ ID NO 1
<211> LENGTH: 4
<212> TYPE: PRT
<213> ORGANISM: Dengue virus
<220> FEATURE:
<221> NAME/KEY: misc_feature
<223> OTHER INFORMATION: DV furin cleavage site in the prM protein

<400> SEQUENCE: 1

Arg Glu Lys Arg
1

<210> SEQ ID NO 2
<211> LENGTH: 12
<212> TYPE: PRT
<213> ORGANISM: Zika virus
<220> FEATURE:
<221> NAME/KEY: misc_feature
<223> OTHER INFORMATION: prM sequence upstream of and including the ZV
      furin recognition site

<400> SEQUENCE: 2

His His Lys Lys Gly Glu Ala Arg Arg Ser Arg Arg
1               5                   10

<210> SEQ ID NO 3
<211> LENGTH: 166
<212> TYPE: PRT
<213> ORGANISM: Dengue virus
<220> FEATURE:
<221> NAME/KEY: misc_feature
<223> OTHER INFORMATION: Wild type DV2 (DENV2) prM

<400> SEQUENCE: 3

Phe His Leu Thr Thr Arg Asn Gly Glu Pro His Met Ile Val Ser Arg
```

```
                1               5                   10                  15
            Gln Glu Lys Gly Lys Ser Leu Leu Phe Lys Thr Glu Asp Gly Val Asn
                            20                  25                  30

Met Cys Thr Leu Met Ala Met Asp Leu Gly Glu Leu Cys Glu Asp Thr
                            35                  40                  45

Ile Thr Tyr Asn Cys Pro Leu Leu Arg Gln Asn Glu Pro Glu Asp Ile
             50                  55                  60

Asp Cys Trp Cys Asn Ser Thr Ser Thr Trp Val Thr Tyr Gly Thr Cys
             65                  70                  75                  80

Thr Thr Thr Gly Glu His Arg Arg Glu Lys Arg Ser Val Ala Leu Val
                            85                  90                  95

Pro His Val Gly Met Gly Leu Glu Thr Arg Thr Glu Thr Trp Met Ser
                            100                 105                 110

Ser Glu Gly Ala Trp Lys His Ala Gln Arg Ile Glu Thr Trp Ile Leu
                            115                 120                 125

Arg His Pro Gly Phe Thr Ile Met Ala Ala Ile Leu Ala Tyr Thr Ile
                            130                 135                 140

Gly Thr Thr Tyr Phe Gln Arg Val Leu Ile Phe Ile Leu Leu Thr Ala
             145                 150                 155                 160

Val Ala Pro Ser Met Thr
                            165

<210> SEQ ID NO 4
            <211> LENGTH: 166
            <212> TYPE: PRT
            <213> ORGANISM: Dengue virus
            <220> FEATURE:
            <221> NAME/KEY: misc_feature
            <223> OTHER INFORMATION: Mutant DENV2 (D2-89R)

<400> SEQUENCE: 4

Phe His Leu Thr Thr Arg Asn Gly Glu Pro His Met Ile Val Ser Arg

```
<212> TYPE: PRT
<213> ORGANISM: Dengue virus
<220> FEATURE:
<221> NAME/KEY: misc_feature
<223> OTHER INFORMATION: Mutant DENV2 (D2-89V)

<400> SEQUENCE: 5

Phe His Leu Thr Thr Arg Asn Gly Glu Pro His Met Ile Val Ser

```
Gly Thr Thr Tyr Phe Gln Arg Val Leu Ile Phe Ile Leu Leu Thr Ala
145                 150                 155                 160

Val Ala Pro Ser Met Thr
                165
```

<210> SEQ ID NO 7
<211> LENGTH: 166
<212> TYPE: PRT
<213> ORGANISM: Dengue virus
<220> FEATURE:
<221> NAME/KEY: misc_feature
<223> OTHER INFORMATION: Mutant DENV2 (D2-89G)

<400> SEQUENCE: 7

```
Phe His Leu Thr Thr Arg Asn Gly Glu Pro His Met Ile Val Ser Arg
1               5                   10                  15

Gln Glu Lys Gly Lys Ser Leu Leu Phe Lys Thr Glu Asp Gly Val Asn
                20                  25                  30

Met Cys Thr Leu Met

-continued

Pro His Val Gly Met Gly Leu Glu Thr Arg Thr Glu Thr Trp Met Ser
            100                 105                 110

Ser Glu Gly Ala Trp Lys His Ala Gln Arg Ile Glu Thr Trp Ile Leu
        115                 120                 125

Arg His Pro Gly Phe Thr Ile Met Ala Ala Ile Leu Ala Tyr Thr Ile
130                 135                 140

Gly Thr Thr Tyr Phe Gln Arg Val Leu Ile Phe Ile Leu Leu Thr Ala
145                 150                 155                 160

Val Ala Pro Ser Met Thr
                165

<210> SEQ ID NO 9
<211> LENGTH: 168
<212> TYPE: PRT
<213> ORGANISM: Zika virus
<220> FEATURE:
<221> NAME/KEY: misc_feature
<223> OTHER INFORMATION: wild type prM amino acid sequence

<400> SEQUENCE: 9

Ala Glu Ile Thr Arg Arg Gly Ser Ala Tyr Tyr Met Tyr Leu Asp Arg
1               5                   10                  15

Ser Asp Ala Gly Lys Ala Ile Ser Phe Ala Thr Thr Leu Gly Val Asn
            20                  25                  30

Lys Cys His Val Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Lys Val Glu Asn Trp
        115                 120                 125

Ile Phe Arg Asn Pro Gly Phe Ala Leu Val Ala Val Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser
                165

<210> SEQ ID NO 10
<211> LENGTH: 4
<212> TYPE: PRT
<213> ORGANISM: Zika virus
<220> FEATURE:
<221> NAME/KEY: misc_feature
<223> OTHER INFORMATION: tetrapeptide site

<400> SEQUENCE: 10

Arg Ser Arg Arg
1

<210> SEQ ID NO 11
<211> LENGTH: 50
<212> TYPE: PRT
<213> ORGANISM: Zika virus

```
<220> FEATURE:
<221> NAME/KEY: misc_feature
<223> OTHER INFORMATION: Wild-type

<400> SEQUENCE: 11

His His Lys Lys Gly Glu Ala Arg Arg Ser Arg Arg Ala Val Thr Leu
1               5                   10                  15

Pro Ser His Ser Thr Arg Lys Leu Gln Thr Arg Ser Gln Thr Trp Leu
                20                  25                  30

Glu Ser Arg Glu Tyr Thr Lys His Ile Lys Val Glu Asn Trp Ile Phe
            35                  40                  45

Arg Asn
    50

<210> SEQ ID NO 12
<211> LENGTH: 50
<212> TYPE: PRT
<213> ORGANISM: Zika virus
<220> FEATURE:
<221> NAME/KEY: misc_feature
<223> OTHER INFORMATION: Mutant

<400> SEQUENCE: 12

His His Lys Lys Gly Glu Ala Arg Arg Arg Arg Ala Val Thr Leu
1               5                   10                  15

Pro Ser His Ser Thr Arg Lys Leu Gln Thr Arg Ser Gln Thr Trp Leu
                20                  25                  30

Glu Ser Arg Glu Tyr Thr Lys His Ile Lys Val Glu Asn Trp Ile Phe
            35                  40                  45

Arg Asn
    50

<210> SEQ ID NO 13
<211> LENGTH: 12
<212> TYPE: PRT
<213> ORGANISM: Zika virus
<220> FEATURE:
<221> NAME/KEY: misc_feature
<223> OTHER INFORMATION: Mutant

<400> SEQUENCE: 13

Thr Thr Thr Gly Glu His Arg Arg Arg Lys Arg Ser
1               5                   10

<210> SEQ ID NO 14
<211> LENGTH: 22
<212> TYPE: PRT
<213> ORGANISM: Zika virus
<220> FEATURE:
<221> NAME/KEY: misc_feature
<223> OTHER INFORMATION: Mutant

<400> SEQUENCE: 14

Thr Thr Thr Gly Glu His Arg Arg Arg Lys Arg Ser Val Ala Leu Val
1               5                   10                  15

Pro His Val Gly Met Gly
                20

<210> SEQ ID NO 15
<211> LENGTH: 37
<212> TYPE: PRT
<213> ORGANISM: Zika virus
<220> FEATURE:
<221> NAME/KEY: misc_feature
```

```
<223> OTHER INFORMATION: ZV M2 Mutant

<400> SEQUENCE: 15

Thr Thr Thr Gly Glu His Arg Arg Arg Lys Arg Ser Val Ala Leu Val
1               5                   10                  15

Pro His Val Gly Met Gly Leu Glu Thr Arg Thr Glu Thr Trp Met Ser
            20                  25                  30

Ser Glu Gly Ala Trp
        35

<210> SEQ ID NO 16
<211> LENGTH: 4
<212> TYPE: PRT
<213> ORGANISM: Artificial Sequence
<220> FEATURE:
<223> OTHER INFORMATION: Synthetic: consensus tetrapeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: X is K or R

<400> SEQUENCE: 16

Arg Xaa Xaa Arg
1

<210> SEQ ID NO 17
<211> LENGTH: 51
<212> TYPE: PRT
<213> ORGANISM: Dengue virus
<220> FEATURE:
<221> NAME/KEY: misc_feature
<223> OTHER INFORMATION: DV1 mutant

<400> SEQUENCE: 17

Cys Ser Gln Thr Gly Glu His Arg Arg Arg Lys Arg Ser Val Ala Leu
1               5                   10                  15

Ala Pro His Val Gly Leu Gly Leu Glu Thr Arg Thr Glu Thr Trp Met
            20                  25                  30

Ser Ser Glu Gly